United States Patent
Nuopponen et al.

(10) Patent No.: US 11,332,714 B2
(45) Date of Patent: May 17, 2022

(54) CELL SYSTEM AND METHOD FOR STORING CELLS

(71) Applicant: UPM-Kymmene Corporation, Helsinki (FI)

(72) Inventors: Markus Nuopponen, Helsinki (FI); Jane Spencer-Fry, Berkshire (GB); Karen Coopman, Leicestershire (GB)

(73) Assignee: UPM-KYMMENE CORPORATION, Helsinki (FI)

( * ) Notice: Subject to any disclaimer, the term of this patent is extended or adjusted under 35 U.S.C. 154(b) by 245 days.

(21) Appl. No.: 16/718,284

(22) Filed: Dec. 18, 2019

(65) Prior Publication Data

US 2020/0199536 A1 Jun. 25, 2020

(30) Foreign Application Priority Data

Dec. 21, 2018 (EP) .................... 18397536

(51) Int. Cl.
*C12N 5/0775* (2010.01)
*A01N 1/02* (2006.01)
*A61K 35/28* (2015.01)

(52) U.S. Cl.
CPC ......... *C12N 5/0662* (2013.01); *A01N 1/0231* (2013.01); *A61K 35/28* (2013.01); *C12N 2500/30* (2013.01); *C12N 2500/32* (2013.01); *C12N 2500/34* (2013.01); *C12N 2533/78* (2013.01)

(58) Field of Classification Search
None
See application file for complete search history.

(56) References Cited

U.S. PATENT DOCUMENTS

| | | | | |
|---|---|---|---|---|
| 5,855,619 | A | * | 1/1999 | Caplan ................ A61L 27/3834 623/23.72 |
| 2018/0024121 | A1 | | 1/2018 | Yliperttula et al. |
| 2018/0094081 | A1 | | 4/2018 | Nuopponen |
| 2019/0039918 | A1 | | 2/2019 | Hartikainen et al. |
| 2019/0336643 | A1 | | 11/2019 | Luukko et al. |
| 2020/0115678 | A1 | | 4/2020 | Nuopponen et al. |
| 2021/0127663 | A1 | | 5/2021 | Paukkonen et al. |
| 2021/0130500 | A1 | | 5/2021 | Vuorinen et al. |

OTHER PUBLICATIONS

Malinen et al. "Differentiation of liver progenitor cell line to functional organotypic cultures in 3D nanofibrillar cellulose and hyaluronan-gelatin hydrogels." Biomaterials 35.19 (2014): 5110-5121 (Year: 2014).*
Lou et al. "The use of nanofibrillar cellulose hydrogel as a flexible three-dimensional model to culture human pluripotent stem cells." Stem Cells and Development 23.4 (2014): 380-392 (Year: 2014).*
Toivonen et al. "Regulation of human pluripotent stem cell-derived hepatic cell phenotype by three-dimensional hydrogel models." Tissue Engineering Part A 22.13-14 (2016): 971-984 (Year: 2016).*
Chennakesava Cuddapah, "Bone marrow derived mesenchymal stem cells cultured in 3D matrix", CeLLnTEC Advanced Cell Systems AG, Oct. 1, 2018; 2 pages. XP-002791549.
Lou, Yan-Ru et al., "The Use of Nanofibrillar Cellulose Hydrogel As a Flexible Three-Dimensional Model to Culture Human Pluripotent Stem Cells", Stem Cells and Development, vol. 23, No. 4, 2014; pp. 380-392.
UPM Biomedicals, "GrowDex—The Natural Choice For Cell Culture", GrowDex brochure, 2018; 6 pages. XP002791550.

* cited by examiner

*Primary Examiner* — Emily A Cordas
(74) *Attorney, Agent, or Firm* — Cantor Colburn LLP

(57) ABSTRACT

The present disclosure provides a cell system comprising eukaryotic cells in a hydrogel comprising nanofibrillar cellulose in cell storage medium at a temperature in the range of 0-25° C. The present disclosure also provides a method for storing eukaryotic cells, the method comprising providing eukaryotic cells, providing nanofibrillar cellulose, combining the cells and the nanofibrillar cellulose to form the cell system, and storing the cell system at a temperature in the range of 0-25° C.

18 Claims, 5 Drawing Sheets

CELL SYSTEM AND METHOD FOR STORING CELLS

CROSS REFERENCE TO RELATED APPLICATIONS

This application claims priority to and the benefit of EP Application No. 18397536.6, filed Dec. 21, 2018, the contents of which are incorporated herein by reference in their entirety.

FIELD OF THE APPLICATION

The present application relates to cell systems comprising nanofibrillar cellulose for storing cells. The present applications also relate to methods for storing cells at hypothermic temperatures. The present application also relates to uses of the cell systems.

BACKGROUND

Stem cells, such as human embryonic stem cells (hESCs) or human induced pluripotent stem cells (hiPSCs), are self-renewing pluripotent cells that are able to differentiate into many cell types in the body. They hold great promises e.g. for cell therapy, drug research and tissue engineering. Further, it is envisioned that in the future human induced pluripotent stem cells, multipotent cells and other undifferentiated cells will be proliferated and directed to differentiate into specific lineages so as to develop differentiated cells or tissues which can be transplanted into human bodies for therapeutic purposes. Human pluripotent stem cells and the differentiated cells that may be derived from them are also powerful scientific tools for studying human cellular and developmental systems.

The medical applications of cell-based therapies are rapidly increasing. Therefore it is desired to develop systems that enable the storage and transportation of cell therapy products from manufacture site to site of use. Freezing and thawing the cells may damage the cells, lower the amount of viable cells, and is time consuming, complex and expensive. There is need for simpler and inexpensive methods for storing cells for a shorter term, for example during transportation.

SUMMARY

In the present invention it was found out that cells, especially stem cells, can be stored in a nanofibrillar cellulose hydrogel at hypothermic temperatures for several days. This can be used for stabilizing the cells for transportation. Herein it is disclosed how to use the nanofibrillar cellulose hydrogel as a matrix for the cells. The matrix provides support for the cells, but it also provides cytoprotective properties, i.e. conditions where the cells remain stable and viable.

In general hypothermic storage may induce adverse effects to the cells, for example hypoxic stress, ischemia and reperfusion injury, disruptions in membrane potential (redox balance), cellular ionic imbalances such as disturbance of $Na^+$, $Ca^{2+}$, and $Fe^{2+}$ homeostasis, generation of reactive oxygen species, collapse of cytoskeleton, and ultrastructural damage. Especially increased hypothermic storage intervals may result in the activation of necrotic or apoptosis cell death pathways. The solutions presented in this disclosure aim to prevent or alleviate these negative effects.

The present disclosure provides a cell system comprising eukaryotic cells in a hydrogel comprising nanofibrillar cellulose in cell storage medium at a temperature in the range of 0-25° C.

The present disclosure also provides a method for storing eukaryotic cells, the method comprising
providing eukaryotic cells,
providing nanofibrillar cellulose,
providing cell storage medium,
combining the cells, the nanofibrillar cellulose and the cell storage medium to form a cell system, and
storing the cell system at a temperature in the range of 0-25° C.

The temperatures used for storing and/or transporting the cells are hypothermic temperatures, which may include ambient temperatures. Hypothermic temperatures as used herein may refer to temperatures which are lower than a body temperature or a temperature used for culturing cells. Hypothermic temperature may refer to a temperature below 37° C., or 30° C. or below, or 25° C. or below, or even lower temperature. However temperatures below 0° C. are not required, which prevents damaging the cells by freezing. As no freezing is carried out, the process is simpler and does not require specific freezing equipment, thawing or for example use of liquid nitrogen. Also no cryoprotectants or lyoprotectants are needed. The cells and the materials are not dried, such as lyophilized, so they do not need to be rehydrated. When using the hypothermic temperatures the cells remain viable and may be used immediately after releasing from the matrix, or already when bound to the matrix, for example to enable quality control testing. The cells may enter pause state, which helps maintaining them in the cell system, especially maintaining them at a desired state.

The present disclosure also provides a method for providing eukaryotic cells, the method comprising
providing the cell system, and
extracting the cells from the hydrogel, such as by enzymatically digesting the hydrogel or by diluting the hydrogel, to provide the cells.

The main embodiments are characterized in the independent claims. Various embodiments are disclosed in the dependent claims. The embodiments and examples recited in the claims and the specification are mutually freely combinable unless otherwise explicitly stated.

The formed cell system enables obtaining a scalable, reproducible and cost-effective cell storage system, wherefrom the cells may be easily released and harvested.

The formed cell system also enables providing a composition for storing cells in an undifferentiated state, i.e. to prevent spontaneous or induced differentiation of cells, especially stem cells. Also the proliferation of the cells may be paused or substantially decreased. For example maintaining stem cells in pluripotent or multipotent state is demanding and requires careful control of storing conditions, materials and handling of the cells.

The nanofibrillar cellulose hydrogel provides a hydrophilic matrix, which is non-toxic, biocompatible and also biodegradable. The matrix can be degraded enzymatically, for example by adding cellulase. On the other hand the hydrogel is stable at physiological conditions, and does not need to be crosslinked by using additional agents. It is also possible to dilute the hydrogel, for example to obtain a dispersion which is no longer in a gel state, which may enable releasing and harvesting the cells, for example by centrifuging or filtering. Use of reactive agents can be avoided, which agents could affect the cells. Cells, especially challenging and/or sensitive cells, can be stored and transported in protective nanofibrillar cellulose hydrogels, and recovered to obtain viable cells.

The feature that the hydrogel can be enzymatically digested is advantageous, especially is the case of stem cells. When a cell system is paused, its biological clock stops; similarly, when frozen. Therefore, a completely new generation of "just-add-water" cell products can be provided, where the supportive NFC matrix can be removed after transportation. This may in return accelerate the cell research, as the research typically requires a lot of currently irreplaceable handwork. Also, transporting and storing ready-to-use cell systems is more affordable, as complex cooling systems would not be required. For example 3D cultivated cell spheroid products can be made directly accessible to researchers without the requirement to seed and grow them first. As 3D spheroids better mimic real tumors, particularly for example if hypoxia is considered, their usage will likely increase in the near future. Later, clinical applications for the cell products can be considered in a more serious manner.

Certain advantageous properties of the hydrogel comprising nanofibrillar cellulose include flexibility, elasticity and remouldability. As the hydrogel contains a lot of water, it may also show good permeability. The hydrogels of the embodiments also provide high water retention capacity and molecule diffusion property speed The hydrogels described herein are useful in medical and scientific applications, wherein the materials comprising nanofibrillar cellulose are in contact with living matter. The products containing nanofibrillar cellulose as described herein are highly biocompatible with the living matter and provide several advantageous effects. Without binding to any specific theory, it is believed that a hydrogel comprising very hydrophilic nanofibrillar cellulose having a very high specific surface area, and thus high water retention ability, when applied against cells and/or tissue, provides favourable moist environment between the cells and/or tissue and the hydrogel comprising nanofibrillar cellulose. The high amount of free hydroxyl groups in the nanofibrillar cellulose forms hydrogen bonds between the nanofibrillar cellulose and water molecules and enables gel formation and the high water retention ability of the nanofibrillar cellulose. Because of the high amount of water in the nanofibrillar cellulose hydrogel, only water is supposed to be in contact with cells or tissue, and which also enables migration of fluids and/or agents if necessary.

The nanofibrillar cellulose used as a matrix for the cells provides an environment, which protects the cells and helps them maintain their viability at challenging conditions, for example when nutrients are not available. One advantage of the nanofibrillar cellulose material is that the dimensions of the fibrillar network of cellulose nanofibers is very close to natural ECM network of collagen nanofibers. Furthermore, cellulose nanofiber is non-animal based material, so there is no risk for disease transfer. Currently, most of the commercial products are isolated from animals. With the present materials it is possible to obtain a transparent and porous matrix for the cells, and the handling of the material is easy compared to the alternatives. Cellulose nanofibers have negligible fluorescence background. Cellulose nanofiber hydrogel has optimal elasticity, stiffness, shear stress, mechanical adhesion and porosity to be used as 3D and 2D cell storage matrix.

DETAILED DESCRIPTION

Figure 1:
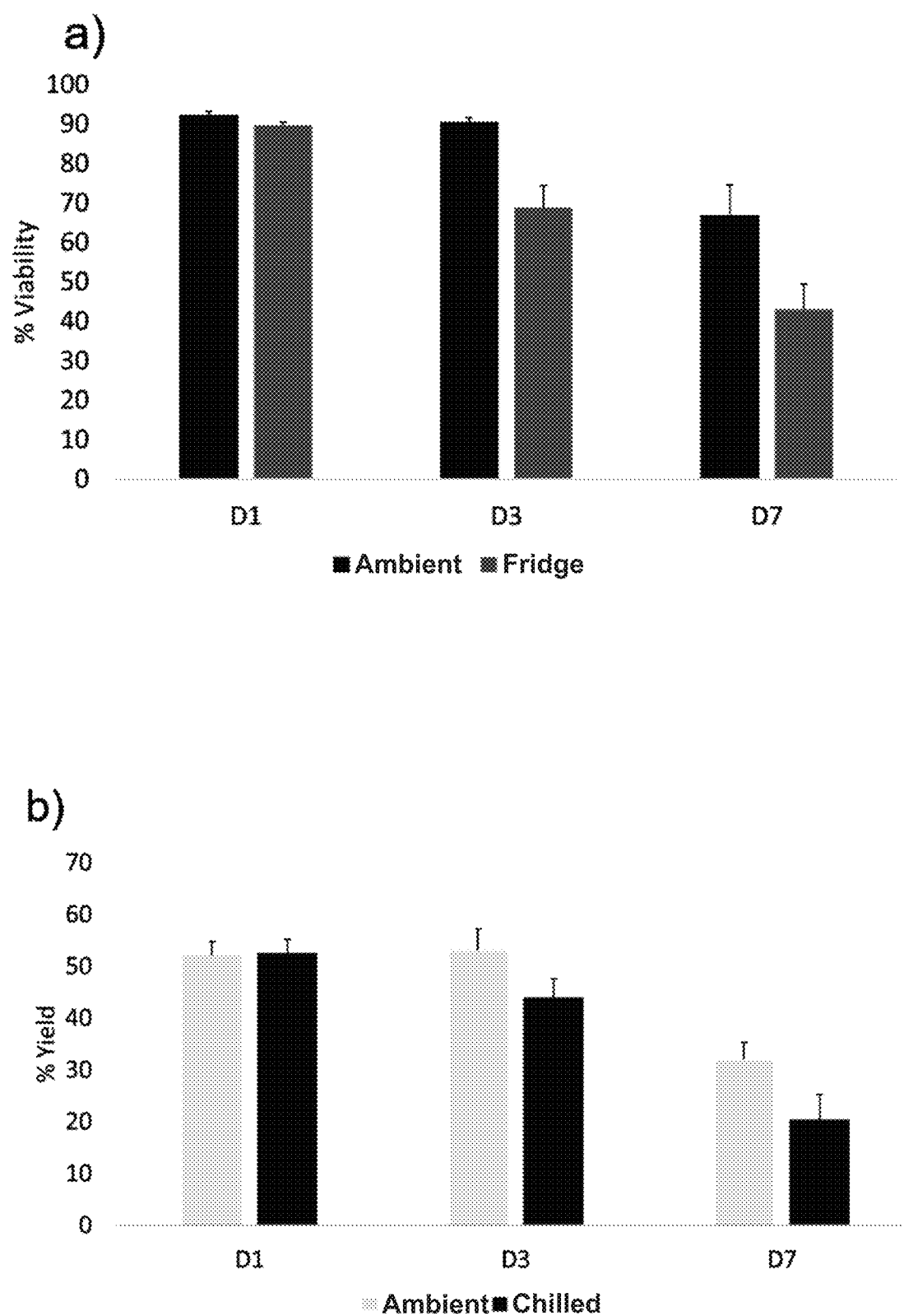
FIG. 1 shows MSCs paused at ambient or refrigerated conditions for up to 7 days in 0.4% gels and recovered using the optimized GrowDase® protocol (2 hours, 1300 µg/mg). Cell viability (a) and yield (b) were calculated. N=3.

In this specification, percentage values, unless specifically indicated otherwise, are based on weight (w/w). If any numerical ranges are provided, the ranges include also the upper and lower values. The open term "comprise" also includes a closed term "consisting of" as one option.

The materials and products described herein may be medical and/or scientific materials and products, such as life science materials and products, and may be used in the methods and the applications involving living cells and/or bioactive material or substances, such as described herein. The materials or products may be cell culture, cell storage and/or cell transport materials or products, and may be used in methods wherein cells are cultured, stored, maintained, transported, provided, modified, tested, and/or used for medical or scientific purposes, or in other related and applicable methods.

In the methods and products disclosed herein specific cells are provided and combined with nanofibrillar cellulosic material. The materials or products may be used to form a cell system described herein. A final product may contain the cells and therefore form the cell system. The cell system may comprise eukaryotic cells in a hydrogel comprising nanofibrillar cellulose, but other cells may be applied as well. The hydrogel may be in a variety of forms, such as continuous, partly or fully discontinuous, for example including a plurality of beads or the like entities in discontinuous form, which entities may be separate or interconnected. However, the structure of the entities is homogenous. The concentration of the nanofibrillar cellulose in the hydrogel may be in the range of 0.1-10%, such as 0.2-5% (w/w), 0.4-2% (w/w), or 0.8-1.5% (w/w).

The present disclosure also provides methods for storing eukaryotic cells, as well as methods for maintaining the cells at a desired state, such as at an undifferentiated state and/or at a paused state, and to methods for transporting or moving the cells, and methods for providing the cells.

Cells

In the present methods and products, cells are provided. The cells may be prokaryotic cells, such as bacterial cells, or they may be eukaryotic cells. Eukaryotic cells may be plant cells, yeast cells or animal cells. Examples of eukaryotic cells include transplantable cells, such as stem cells. The cells may be animal cells or human cells.

Specific examples of cells include stem cells, undifferentiated cells, precursor cells, as well as fully differentiated cells and combinations thereof. In some examples the cells comprise cell types selected from the group consisting of keratocytes, keratinocytes, fibroblast cells, epithelial cells and combinations thereof. In some examples the cells are selected from the group consisting of stem cells, progenitor cells, precursor cells, connective tissue cells, epithelial cells, muscle cells, neuronal cells, endothelial cells, fibroblasts, keratinocytes, smooth muscle cells, stromal cells, mesenchymal cells, immune system cells, hematopoietic cells, dendritic cells, hair follicle cells and combinations thereof. The cells may be tumor or cancer cells, genetically modified cells, such as transgenic cells, cisgenic cells or knock-out cells, or pathogenic cells. Such cells may be used for example for drug research or in therapy. Especially stem cells may be used in therapeutical applications, for example provided to a patient.

In one embodiment the cells are eukaryotic cells, such as mammalian cells. Examples of mammalian cells include human cells, mouse cells, rat cells, rabbit cells, monkey cells, pig cells, bovine cells, chicken cells and the like. It is to be noted that even though the advantages of the present methods and products are best demonstrated for storing mammalian cells, the methods and products may be also used for storing other cells, such as non-mammalian eukaryotic cells, yeast cells, or prokaryotic cells.

In one embodiment the cells are stem cells, such as omnipotent, pluripotent, multipotent, oligopotent or unipotent stem cells. Stem cells are cells capable of renewing themselves through cell division and can differentiate into multi-lineage cells. These cells may be categorized as embryonic stem cells (ESCs), induced pluripotent stem cells (iPSCs), and adult stem cells, also called as tissue-specific or somatic stem cells. The stem cells may be human stem cells, which may be of non-embryonic origin, such as adult stem cells. These are undifferentiated cells found throughout the body after differentiation. They are responsible for e.g. organ regeneration and capable of dividing in pluripotent or multipotent state and differentiating into differentiated cell lineages. The stem cells may be human embryonic stem cell lines generated without embryo destruction, such as described for example in Cell Stem Cell. 2008 Feb. 7; 2(2):113-7. The stem cells may be obtained from a source of autologous adult stem cells, such as bone marrow, adipose tissue, or blood.

Examples of stem cells include mesenchymal stem cells (MSC), multipotent adult progenitor cells (MAPCO), induced pluripotent stem cells (iPS), and hematopoietic stem cells.

In case of human stem cells the cells may be non-embryonic cells or cells, such as hESCs, which can be derived without destroying the embryo. In case of human embryonic stem cells the cells may be from a deposited cell line or made from unfertilized eggs, i.e. "parthenote" eggs or from parthenogenetically activated ovum, so that no human embryos are destroyed.

In one embodiment the cells are mesenchymal stem cells (MSC). Mesenchymal stem cells (MSCs) are adult stem cells which can be isolated from human and animal sources, such as from mammals. Mesenchymal stem cells are multipotent stromal cells that can differentiate into a variety of cell types, including osteoblasts, chondrocytes, myocytes and adipocytes. Mesenchyme itself is embryonic connective tissue that is derived from the mesoderm and that differentiates into hematopoietic and connective tissue. However mesenchymal stem cells do not differentiate into hematopoietic cells. The terms mesenchymal stem cell and marrow stromal cell have been used interchangeably for many years, but neither term is sufficiently descriptive. Stromal cells are connective tissue cells that form the supportive structure in which the functional cells of the tissue reside. While this is an accurate description for one function of MSCs, the term fails to convey the relatively recently discovered roles of MSCs in the repair of tissue. The term encompasses multipotent cells derived from other non-marrow tissues, such as placenta, umbilical cord blood, adipose tissue, adult muscle, corneal stroma or the dental pulp of deciduous baby teeth. The cells do not have the capacity to reconstitute an entire organ The International Society for Cellular Therapy has proposed minimum criteria to define MSCs. These cells (a) should exhibits plastic adherence, (b) possess specific set of cell surface markers, i.e. cluster of differentiation (CD)73, D90, CD105 and lack expression of CD14, CD34, CD45 and human leucocyte antigen-DR (HLA-DR) and (c) have the ability to differentiate in vitro into adipocyte, chondrocyte and osteoblast. These characteristics are valid for all MSCs, although few differences exist in MSCs isolated from various tissue origins. MSCs are present not only in fetal tissues but also in many adult tissues with few exceptions. Efficient population of MSCs has been reported from bone marrow. Cells which exhibits characteristics of MSCs have been isolated from adipose tissue, amniotic fluid, amniotic membrane, dental tissues, endometrium, limb bud, menstrual blood, peripheral blood, placenta and fetal membrane, salivary gland, skin and foreskin, sub-amniotic umbilical cord lining membrane, synovial fluid and Wharton's jelly.

Human mesenchymal stem cells (hMSC) display a very high degree of plasticity and are found in virtually all organs with the highest density in bone marrow. hMSCs serve as renewable source for mesenchymal cells and have pluripotent ability of differentiating into several cell lineages, including osteoblasts, chondrocytes, adipocytes, skeletal and cardiac myocytes, endothelial cells, and neurons in vitro upon appropriate stimulation, and in vivo after transplantation.

In one example the cells are multipotent adult progenitor cells (MAPC), which are derived from a primitive cell population that can be harvested from bone marrow, muscle and brain. MAPC are a more primitive cell population than mesenchymal stem cells, whilst they imitate embryonic stem cells characteristics they still retain adult stem cells potential in cell therapy. In vitro, MAPC demonstrated a vast differentiation potential to adipogenic, osteogenic, neurogenic, hepatogenic, hematopoietic, myogenic, chondrogenic, epithelial, and endothelial lineages. A key feature of MAPC is that they show large proliferative potential in vitro without losing their phenotype. MAPC may be used for treating a variety of diseases such as ischaemic stroke, graft versus host disease, acute myocardial infarct, organ transplant, bone repair and myelodysplasia. MAPC also enhance bone formation, promote neovascularisation, and have immunomodulatory effects.

Induced pluripotent stem cells (iPS) are a type of pluripotent stem cell that can be generated directly from adult cells. They can propagate practically indefinitely and may give rise to every other cell type in the body, including neurons, heart, pancreatic and liver cells. Induced pluripotent stem cells can be derived directly from adult tissues and they can be made in a patient-matched manner so they may be provided a transplants without the risk of immune rejection. Human induced pluripotent stem cells are of special interest, and they can be generated from for example human fibroblasts, keratinocytes, peripheral blood cells, renal epithelial cells or other suitable cell types.

Hematopoietic stem cells (HSCs), also called as blood stem cells, are cells that can develop into all types of blood cells, including white blood cells, red blood cells, and platelets. Hematopoietic stem cells are found in the peripheral blood and the bone marrow. HSCs give rise to both the myeloid and lymphoid lineages of blood cells. Myeloid and lymphoid lineages both are involved in dendritic cell formation. Myeloid cells include monocytes, macrophages, neutrophils, basophils, eosinophils, erythrocytes, and megakaryocytes to platelets. Lymphoid cells include T cells, B cells, and natural killer cells. Hematopoietic stem cell transplants can be used in the treatment of cancers and other immune system disorders.

In general the cells may be cultured in a hydrogel, and they may be also stored in it. The cells can be maintained and proliferated on or in the hydrogel without animal or human based agents or medium originating outside the cells. The cells may be evenly dispersed on or in the hydrogel.

Initially the cells may be pre-cultured in a separate culture, and recovered and transferred into a new medium, which may be similar or different than the culture medium. A cell suspension is obtained. This, or another cell suspension, may be combined and/or mixed with the nanofibrillar cellulose, such as a hydrogel comprising nanofibrillar cellulose, to obtain or form a cell system. If cells are cultured in the cell system a cell culture is formed. The cell system or culture may be 2D system or culture or a 3D system or culture. 2D system or culture refers to a system or culture in a membrane and/or as a layer. 3D system or culture refers to a system or culture in the nanofibrillar cellulose, wherein the cells are permitted to grow and/or interact in all three dimensions. The NFC hydrogel matrix mimics the natural extracellular matrix structure and provides efficient transport of nutrients, gases and the like. In one example the cell system is a 3D cell system.

Nanofibrillar Cellulose

The starting material for forming the cell system is nanofibrillar cellulose, also called as nanocellulose, which refers to isolated cellulose fibrils or fibril bundles derived from cellulose raw material. Nanofibrillar cellulose is based on a natural polymer that is abundant in nature. Nanofibrillar cellulose has a capability of forming viscous hydrogel in water. Nanofibrillar cellulose production techniques may be based on disintegrating fibrous raw material, such as grinding of aqueous dispersion of pulp fibers to obtain nanofibrillated cellulose. After the grinding or homogenization process, the obtained nanofibrillar cellulose material is a dilute viscoelastic hydrogel.

The obtained material usually exists at a relatively low concentration homogeneously distributed in water due to the disintegration conditions. The starting material may be an aqueous gel at a concentration of 0.2-10% (w/w), for example 0.2-5% (w/w). The nanofibrillar cellulose may be obtained directly from the disintegration of fibrous raw material.

Because of its nanoscale structure nanofibrillar cellulose has unique properties which enable functionalities which cannot be provided by conventional cellulose. However, because of the nanoscale structure nanofibrillar cellulose is also a challenging material. For example dewatering or handling of nanofibrillar cellulose may be difficult.

The nanofibrillar cellulose may be prepared from cellulose raw material of plant origin, or it may also be derived from certain bacterial fermentation processes. The nanofibrillar cellulose is preferably made of plant material. The raw material may be based on any plant material that contains cellulose. In one example the fibrils are obtained from non-parenchymal plant material. In such case the fibrils may be obtained from secondary cell walls. One abundant source of such cellulose fibrils is wood fibres. The nanofibrillar cellulose may be manufactured by homogenizing wood-derived fibrous raw material, which may be chemical pulp. Cellulose fibers are disintegrated to produce fibrils which have an average diameter of only some nanometers, which may be 200 nm or less in most cases, and gives a dispersion of fibrils in water. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging. In general in the cellulose sources from primary cell walls, such as sugar beet, potato tuber and banana rachis, the microfibrils are easier to liberate from the fibre matrix than fibrils from wood, and the disintegration requires less energy. However, these materials are still somewhat heterogeneous and consist of large fibril bundles.

Non-wood material may be from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. The cellulose raw material could be also derived from the cellulose-producing micro-organism. The micro-organisms can be of the genus *Acetobacter, Agrobacterium, Rhizobium, Pseudomonas or Alcaligenes*, preferably of the genus *Acetobacter* and more preferably of the species *Acetobacter xylinum* or *Acetobacter pasteurianus*.

It was found out that nanofibrillar cellulose obtained from wood cellulose is preferable for medical or scientific products described herein. Wood cellulose is available in large amounts, and the preparation methods developed for wood cellulose enable producing nanofibrillar materials suitable for the products. The nanofibrillar cellulose obtained by fibrillating plant fibers, especially wood fibers, differs structurally from nanofibrillar cellulose obtained from microbes, and it has different properties. For example compared to bacterial cellulose, nanofibrillated wood cellulose is homogenous and more porous and loose material, which is advantageous in applications involving living cells. Bacterial cellulose is usually used as such without similar fibrillation as in plant cellulose, so the material is different. Bacterial cellulose is dense material which easily forms small spheroids and therefore the structure of the material is discontinuous, and it is not desired to use such material in the applications relating to living cells.

Wood may be from softwood tree such as spruce, pine, fir, larch, douglas-fir or hemlock, or from hardwood tree such as birch, aspen, poplar, alder, *eucalyptus*, oak, beech or acacia, or from a mixture of softwoods and hardwoods. In one example the nanofibrillar cellulose is obtained from wood pulp. The nanofibrillar cellulose may be obtained from hardwood pulp. In one example the hardwood is birch. The nanofibrillar cellulose may be obtained from softwood pulp. In one example said wood pulp is chemical pulp. Chemical pulp may be desired for the products. Chemical pulp is pure material and may be used in a wide variety of applications. For example chemical pulp lack the pitch and resin acids present in mechanical pulp, and it is more sterile or easily sterilisable. Further, chemical pulp is more flexible and provides advantageous properties for example in medical materials, membranes, patches, dressings and other materials, which may be applied on living tissue.

As used herein, the term "nanofibrillar cellulose" refers to cellulose fibrils and/or fibril bundles separated from cellulose-based fiber raw material. These fibrils are characterized by a high aspect ratio (length/diameter). The average length of nanofibrillar cellulose (the median length of particles such as fibrils or fibril bundles) may exceed 1 µm, and in most cases it is 50 µm or less. If the elementary fibrils are not completely separated from each other, the entangled fibrils may have an average total length for example in the range of 1-100 µm, 1-50 µm, or 1-20 µm. However, if the nanofibrillar material is highly fibrillated, the elementary fibrils may be completely or almost completely separated and the average fibril length is shorter, such as in the range of 1-10 µm or 1-5 µm. This applies especially for native grades of fibrils which are not shortened or digested, for example chemically, enzymatically or mechanically. However, strongly derivatized nanofibrillar cellulose may have a shorter average fibril length, such as in the range of 0.3-50 µm, such as 0.3-20 µm, for example 0.5-10 µm or 1-10 µm. Especially shortened fibrils, such as enzymatically or chemically digested fibrils, or mechanically treated material, may have an average fibril length of less than 1 µm, such as 0.1-1 µm, 0.2-0.8 µm or 0.4-0.6 µm. The fibril length and/or diameter may be estimated microscopically, for example using CRYO-TEM, SEM or AFM images.

The average diameter (width) of nanofibrillar cellulose is less than 1 µm, or 500 nm or less, such as in the range of 1-500 nm, but preferably 200 nm or less, even 100 nm or less or 50 nm or less, such as in the range of 1-200 nm, 2-200 nm, 2-100 nm, or 2-50 nm, even 2-20 for highly fibrillated material. The diameters disclosed herein may refer to fibrils and/or fibril bundles. The smallest fibrils are in the scale of elementary fibrils, the average diameter being typically in the range of 2-12 nm. The dimensions and size distribution of the fibrils depend on the refining method and efficiency. In case of highly refined native nanofibrillar cellulose, the average diameter of a fibril may be in the range of 2-200 nm or 5-100 nm, for example in the range of 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose obtained from plants, especially wood, may also contain small amounts of other plant components, especially wood components, such as hemicellulose or lignin. The amount is dependent on the plant source.

In general cellulose nanomaterials may be divided into categories according to TAPPI W13021, which provides standard terms for cellulose nanomaterials. Not all of these materials are nanofibrillar cellulose. Two main categories are "Nano objects" and "Nano structured materials". Nanostructured materials include "Cellulose microcrystals" (sometimes called as CMC) having a diameter of 10-12 µm and length:diameter ratio (L/D)<2, and "Cellulose microfibrils" having a diameter of 10-100 nm and a length of 0.5-50 µm. Nano objects include "Cellulose nanofibers", which can be divided into "Cellulose nanocrystals" (CNC) having a diameter of 3-10 nm and L/D>5, and "Cellulose nanofibrils" (CNF or NFC), having a diameter of 5-30 nm and L/D>50.

Different grades of nanofibrillar cellulose may be categorized based on three main properties: (i) size distribution, length and diameter (ii) chemical composition, and (iii) rheological properties. To fully describe a grade, the properties may be used in parallel. Examples of different grades include native (or non-modified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low degree of substitution, low viscosity vs. high viscosity etc. The fibrillation technique and the chemical pre-modification have an influence on the fibril size distribution. Typically, non-ionic grades have wider average fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood vs. softwood pulp, different polysaccharide composition exists in the final nanofibrillar cellulose product. Commonly, the non-ionic grades are prepared from bleached birch pulp, which yields high xylene content (25% by weight). Modified grades are prepared either from hardwood or softwood pulps. In those modified grades, the hemicelluloses are also modified together with the cellulose domain. Most probably, the modification is not homogeneous, i.e. some parts are more modified than others. Thus, detailed chemical analysis is usually not possible as the modified products are complicated mixtures of different polysaccharide structures.

In an aqueous environment, a dispersion of cellulose nanofibers forms a viscoelastic hydrogel network. The gel is formed already at relatively low concentrations of for example 0.05-0.2% (w/w) by dispersed and hydrated entangled fibrils. The viscoelasticity of the NFC hydrogel may be characterized for example with dynamic oscillatory rheological measurements.

The nanofibrillar cellulose hydrogels exhibit characteristic rheological properties. For example they are shear-thinning or pseudoplastic materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent for example on the raw material, the disintegration method and number of disintegration runs. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration treatment is performed at conditions wherein water is sufficiently present to prevent the formation of bonds between the fibers.

In one example the disintegration is carried out by using a disperser having at least one rotor, blade or similar moving mechanical member, such as a rotor-rotor dispergator, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives a plurality of successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor dispergator the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor dispergator is an Atrex® device.

Another example of a device suitable for disintegrating is a pin mill, such as a multi-peripheral pin mill. One example of such device includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one example the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The expressions "disintegration" or "disintegration treatment" may be used interchangeably with "fibrillation".

The fiber material dispersion that is subjected to fibrillation is a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be for example Brookfield viscosity or zero shear viscosity. The specific viscosity, as described herein, distinguishes nanofibrillar cellulose from non-nanofibrillar cellulose.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C., heated if necessary and mixed. A low rotational speed 10 rpm is used. In general Brookfield viscosity may be measured at 20° C.±1° C., at a consistency of 0.8% (w/w) and at 10 rpm.

The nanofibrillar cellulose provided as a starting material in the method may be characterized by the viscosity it provides in a water solution. The viscosity describes, for example, the fibrillation degree of the nanofibrillar cellulose. In one example the nanofibrillar cellulose when dispersed in water provides a Brookfield viscosity of at least 2000 mPa·s, such as at least 3000 mPa·s, measured at 20° C.±1° C., at a consistency of 0.8% (w/w) and at 10 rpm. In one example the nanofibrillar cellulose, when dispersed in water, provides a Brookfield viscosity of at least 10000 mPa·s measured at 20° C.±1° C., at a consistency of 0.8% (w/w) and at 10 rpm. In one example the nanofibrillar cellulose, when dispersed in water, provides a Brookfield viscosity of at least 15000 mPa·s measured at 20° C.±1° C., at a consistency of 0.8% (w/w) and at 10 rpm. Examples of Brookfield viscosity ranges of said nanofibrillar cellulose when dispersed in water include 2000-20000 mPa·s, 3000-20000 mPa·s, 10000-20000 mPa·s, 15000-20000 mPa·s, 2000-25000 mPa·s, 3000-25000 mPa·s, 10000-25000 mPa·s, 15000-25000 mPa·s, 2000-30000 mPa·s, 3000-30000 mPa·s, 10000-30000 mPa·s, and 15000-30000 mPa·s, measured at 20° C.±1° C., at a consistency of 0.8% (w/w) and at 10 rpm.

Nanofibrillar cellulose may be or comprise non-modified nanofibrillar cellulose. The drainage of non-modified nanofibrillar cellulose is significantly faster than for example anionic grade. Non-modified nanofibrillar cellulose generally has a Brookfield viscosity in the range of 2000-10000 mPa·s, measured at a consistency of 0.8% (w/w) and at 10 rpm. However, in the present methods non-modified nanofibrillar cellulose does not crosslink efficiently because it contains a low amount of free carboxylic groups required for the crosslinking with the multivalent ions. It is preferred that the nanofibrillar cellulose has a suitable carboxylic acid content, such as in the range of 0.6-1.4 mmol COOH/g, for example in the range of 0.7-1.2 mmol COOH/g, or in the range of 0.7-1.0 mmol COOH/g or 0.8-1.2 mmol COOH/g, determined by conductometric titration.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, i.e. pulp.

The modification treatment to the fibers may be chemical, enzymatic or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface.

The cellulose in the fibers may be especially ionically charged after the modification. The ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonization and carboxymethylation. Chemical modifications introducing groups, such as carboxyl groups, which may take part in forming a covalent bond between the nanofibrillar cellulose and the bioactive molecule, may be desired. A cationic charge in turn may be created chemically by cationization by attaching a cationic group to the cellulose, such as quaternary ammonium group.

Nanofibrillar cellulose may comprise chemically modified nanofibrillar cellulose, such as anionically modified nanofibrillar cellulose or cationically modified nanofibrillar cellulose. In one example the nanofibrillar cellulose is anionically modified nanofibrillar cellulose. In one example the anionically modified nanofibrillar cellulose is oxidized nanofibrillar cellulose. In one example the anionically modified nanofibrillar cellulose is sulphonized nanofibrillar cellulose. In one example the anionically modified nanofibrillar cellulose is carboxymethylated nanofibrillar cellulose. The material obtained with the anionical modification of cellulose may be called anionic cellulose, which refers to material wherein the amount or proportion of anionic groups, such as carboxylic groups, is increased by the modification, when compared to a non-modified material. It is also possible to introduce other anionic groups to the cellulose, instead or in addition to carboxylic groups, such as phosphate groups or sulphate groups. The content of these groups may be in the same ranges as is disclosed for carboxylic acid herein.

The cellulose may be oxidized. In the oxidation of cellulose, the primary hydroxyl groups of cellulose may be oxidized catalytically by a heterocyclic nitroxyl compound, such as through N-oxyl mediated catalytic oxidation, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. Regarding the finding that low degree of oxidation does not allow efficient enough fibrillation and higher degree of oxidation inflicts degradation of cellulose after mechanical disruptive treatment, the cellulose may be oxidized to a level having a carboxylic acid content in the oxidized cellulose in the range of 0.5-2.0 mmol COOH/g pulp, 0.6-1.4 mmol COOH/g pulp, or 0.8-1.2 mmol COOH/g pulp, preferably to 1.0-1.2 mmol COOH/g pulp, determined by conductometric titration. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

The modifications of nanofibrillar cellulose disclosed herein may also be applied to other fibrillar cellulose grades described herein. For example also highly refined cellulose or microfibrillar cellulose may be similarly chemically or enzymatically modified. However, there are differences for example in the final fibrillation degree of the materials.

In one example such chemically modified nanofibrillar cellulose, when dispersed in water, provides a Brookfield viscosity of at least 10000 mPa·s measured at 20° C.±1° C., at a consistency of 0.8% (w/w) and at 10 rpm. In one example such chemically modified nanofibrillar cellulose, when dispersed in water, provides a Brookfield viscosity of at least 15000 mPa·s measured at 20° C.±1° C., at a consistency of 0.8% (w/w) and at 10 rpm. In one example such chemically modified nanofibrillar cellulose, when dispersed in water, provides a Brookfield viscosity of at least 18000 mPa·s measured at a consistency of 0.8% (w/w) and at 10 rpm. Examples of anionic nanofibrillar celluloses used have a Brookfield viscosity in the range of 13000-15000 mPa·s or 18000-20000 mPa·s, or even up to 25000 mPa·s, depending on the degree of fibrillation.

In one example the nanofibrillar cellulose is TEMPO oxidized nanofibrillar cellulose. It provides high viscosity at low concentrations, for example a Brookfield viscosity of at least 20000 mPa·s, even at least 25000 mPa·s, measured at a consistency of 0.8% (w/w) and at 10 rpm. In one example the Brookfield viscosity of TEMPO oxidized nanofibrillar cellulose is in the range of 20000-30000 mPa·s, such as 25000-30000 mPa·s, measured at 20° C.±1° C., at a consistency of 0.8% (w/w) and at 10 rpm.

In one example the nanofibrillar cellulose comprises chemically unmodified nanofibrillar cellulose. In one example such chemically unmodified nanofibrillar cellulose, when dispersed in water, provides a Brookfield viscosity of at least 2000 mPa·s, or at least 3000 mPa·s, measured at 20° C.±1° C., at a consistency of 0.8% (w/w) and at 10 rpm.

The nanofibrillar cellulose may also be characterized by the average diameter (or width), or by the average diameter together with the viscosity, such as Brookfield viscosity or zero shear viscosity. In one example nanofibrillar cellulose suitable for use in the products described herein has an average diameter of a fibril in the range of 1-200 nm, or 1-100 nm. In one example said nanofibrillar cellulose has an average diameter of a fibril in the range of 1-50 nm, such as 2-20 nm or 5-30 nm. In one example said nanofibrillar cellulose has an average diameter of a fibril in the range of 2-15 nm, such as in the case of TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

In one example a rheometer viscosity of the nanofibrillar cellulose dispersion is measured at 22° C. with a stress controlled rotational rheometer (AR-G2, TA Instruments, UK) equipped with a narrow gap vane geometry (diameter 28 mm, length 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/ shear rate) at a certain shear stress is recorded after reaching a constant shear rate or after a maximum time of 2 min. The measurement is stopped when a shear rate of 1000 s$^{-1}$ is exceeded. This method may be used for determining the zero-shear viscosity.

In one example the nanofibrillar cellulose, when dispersed in water, provides a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium at 20° C.±1° C. Such nanofibrillar cellulose may also have an average diameter of a fibril of 200 nm or less, such as in the range of 1-200 nm.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH® P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at measured at 20° C.±1° C. a consistency of 0.1% (w/w) in aqueous medium, and measured by nephelometry. To characterize the nanofibrillar cellulose these ranges may be combined with the viscosity ranges of the nanofibrillar cellulose, such as nanofibrillar cellulose which, when dispersed in water, provides a Brookfield viscosity of at least 2000 mPa·s, at least 3000 mPa·s, at least 5000 mPa·s, such as at least 10000 mPa·s, for example at least 15000 mPa·s measured at measured at 20° C.±1° C., at a consistency of 0.8% (w/w) and at 10 rpm.

Auxiliary agents for enhancing the manufacturing process or improving or adjusting the properties of the product may be included in the nanofibrillar cellulose dispersion. Such auxiliary agents may be soluble in the liquid phase of the dispersion, they may form an emulsion or they may be solid. Auxiliary agents may be added already during the manufacturing of the nanofibrillar cellulose dispersion to the raw material or they may be added to a formed nanofibrillar cellulose dispersion or gel. The auxiliary agents may be also added to the final product, for example by impregnating, spraying, dipping, soaking or the like method. The auxiliary agents are usually not covalently bound to the nanofibrillar cellulose, so they may be releasable from the nanocellulose matrix. A controlled and/or sustained release of such agents may be obtained when using NFC as matrix. Examples of auxiliary agents include therapeutic (pharmaceutic) and cosmetic agents and other agents affecting to the properties of the product or to the properties of the active agents, such as buffers, surfactants, plasticizers, emulsifiers or the like. In one example the dispersion contains one or more salts, which may be added to enhance the properties of the final product or to facilitate water removal from the product in the manufacturing process. One example of the salt is sodium chloride. The salt may be included in an amount in the range of 0.01-1.0% (w/w) of the dry matter in the dispersion. The final product may also be dipped or soaked in a solution of sodium chloride, such as in an aqueous solution of about 0.9% sodium chloride. Desired sodium chloride content in the final product may be in the range of 0.5-1%, such as about 0.9%, of the volume of the wet product. The salts, buffers and the like agents may be provided to obtain physiological conditions.

The nanofibrillar cellulose material may be provided as hydrogel, to which the cells are to be combined. The hydrogel may be present in any of the forms described herein.

Hydrogels

Nanofibrillar cellulose, when not completely dewatered, may have a moisture content in the range of 80-99.9% (w/w), or 50-99.8% (w/w). When the nanofibrillar cellulose is present as a gel, it may have a moisture content in the range of 90-99.8% (w/w). The gel may be called as hydrogel.

The nanofibrillar cellulose may be provided in gel form, more particularly as a medical hydrogel. The gel may be mouldable and it may be applied or formed onto a target, such as to cell culture plate, multi-well plate, vial or other container, whereto it may be attached. The target may be also an individual in need of therapy by using the cells included or encapsulated in the hydrogel, such as stem cells.

One example provides a method for preparing such a hydrogel, the method comprising
  providing pulp,
  disintegrating the pulp until nanofibrillar cellulose is obtained,
  forming the nanofibrillar cellulose into a hydrogel The nanofibrillar cellulose may be fibrillated into a desired fibrillation degree and adjusted into desired water content, or otherwise modified, so that it forms a gel having desired properties as described herein. In one example the nanofibrillar cellulose in the hydrogel is anionically modified nanofibrillar cellulose.

The hydrogel to be used as a medical or scientific hydrogel needs to be homogenous. Therefore the method for preparing the hydrogel may include homogenizing a hydrogel comprising nanofibrillar cellulose, preferably with a homogenizing device such as ones described herein. With this preferably non-fibrillating homogenizing step it is possible to remove areas of discontinuity from the gel. A homogenous gel having better properties for the applications is obtained. The hydrogel may be further sterilized, for example by using heat and/or radiation, and/or by adding sterilizing agents, such as antimicrobials.

The nanofibrillar cellulose provided for preparing the cell system may have an initial water content in the range of 80-99.9% (w/w), or 50-99.8% (w/w), such as 90-99.8% (w/w). The material may or may not be in a gel form. More dewatered material may be provided, which facilitates storing, and such material usually needs rehydrating prior to use. Water or cell storage medium may be added.

Cell System

The cell system may be formed by combining the cells and nanofibrillar cellulose, such as hydrogel comprising nanofibrillar cellulose. The cells may be included or encapsulated in the hydrogel, and both terms may be used interchangeably. The cells may be provided in a suspension, and combined with nanofibrillar cellulose to form a hydrogel comprising the cells.

The hydrogel may be also called as cell storage material. The cell system refers to an entity containing the cells and the matrix comprising nanofibrillar cellulose in suitable form, wherein the cell system may be stored and/or transferred from a first location to a second location. The cell system may be included in a container and/or a package. For example the cell system may be applied or provided in a vial, plate, multi-well plate, test tube, bottle or other suitable container. The container may be sealed, for example covered with a sealing membrane or packed in a plastic bag, wrapping or the like. The cell system may be protected from light with the sealing or a package, especially if any light sensitive agents are used in the cell storage medium. The cell system contains liquid cell storage medium. In general the nanofibrillar cellulose contains a large amount of liquid, and it is possible to provide the matrix also as separate entities which are further suspended into the liquid medium.

Different cell system materials may be prepared and provided. These materials may be used for storing, transporting and providing different types of cells in different methods. Storing the cells also enables quality control, especially when the cells are waiting for approval to release.

The cell system comprises cell storage medium, which may be also called as pausing medium, which may be different from cell culture medium. The cell storage medium comprises one or more buffering agent(s). In one embodiment a cell storage medium comprises zwitterionic buffering agent, such as 4-(2-hydroxyethyl)-1-piperazineethanesulfonic acid (HEPES) which was found advantageous in the tests. The buffering agent(s) should preferably have a $pK_a$ value in the range of 6-8.

Cells can be stored and/or controlled in NFC hydrogels for long time, for example for 2-7 days or even longer up to 14 or 21 days. The cell system may be provided at hypothermic temperature, as disclosed herein.

Preferably the cell system is provided at a temperature in the range of 0-30° C., such as 0-25° C. When forming the cell system, the nanofibrillar cellulose material may be provided in a form of a hydrogel and/or a dispersion at the desired temperature and/or the cells, which may be present as a suspension, may be provided at the desired temperature. The method for preparing the cell system may comprise cooling the nanofibrillar cellulose hydrogel and/or dispersion to the desired temperature and/or cooling the cell suspension to the desired temperature. The method may also comprise cooling the formed cell system to the desired temperature.

The temperature is selected in such way that the cells are not frozen, preferably at least 0° C., 1° C. or 2° C., such as in the range of 1-25° C. or 2-25° C. Further, too high temperatures should also be avoided, especially in the case of sensitive cells, such as stem cells, which need to be maintained at an undifferentiated state. Refrigerated temperatures, such as in the range of 1-10° C., for example about 4° C., may be used. However, it may be difficult to maintain such a temperature in cases where the cells are transported by mail delivery or the like. It was found out that the cells, even stem cells, remain viable at ambient temperatures, such as room temperatures even up to 25° C. In one embodiment the temperature is in the range of 10-25° C., or 15-25° C., such as 18-23° C. The desired temperatures can be maintained during the storage and transport by simply using isolated package, preferably containing ice, such as Styrofoam package, or by using a refrigerated box, or the like. During storage the cell system may be stored in a refrigerator or even at room temperature.

The present disclosure provides a cell storage or cell delivery composition, material or matrix comprising the nanofibrillar cellulose product, such as in a form of a hydrogel, bodies or a membrane in wet state. The cell storage material may be provided at a first water content, and aqueous liquid may be added to the material to obtain a second water content. The wet state may refer to the first or the second water content. The second water content may be the water content the cell system, such as during storage or delivering the cells. The first water content may be the water content of the product or material described herein, such as water content below 20%. The second water content may be a water content of 90% or more, such as 95% or more, 98% or more, or 99% or more, which may be considered as hydrogels. The added aqueous liquid may be cell storage medium. Cell culture medium is an aqueous medium used in the cell culture. The cell storage medium is preferably different from cell culture medium. When the cells are applied to the cell storage material i.e. to the hydrogel, the cell culture medium may be exchanged to cell storage medium. The cell storage material may already contain cell storage medium, more particularly the hydrogel may be based on the cell storage medium. The cells may be washed with the cell storage medium before applied to the cell storage material. The cells may be cultured in the hydrogel, and the cell culture medium is exchanged into cell storage medium while the cells are present in the hydrogel. This may be carried our for example by soaking the hydrogel in the cell storage medium.

The cell storage medium may or may not contain agents that are usually included in cell culture medium, such as serum or components thereof. The cell storage medium aims to maintain the ionic and osmotic balances, inhibit acidosis and/or prevent cell swelling at low temperatures. These features facilitate preservation of cell homeostasis, which is not achievable when using just culture medium as a preservation formulation. One example of cell storage medium is a buffer solution, especially buffer-salt-solution, for example isotonic buffer, such as phosphate buffered saline. At the simples the cell storage medium contains only one or more buffering agent(s) and optionally one or more salt(s). The cell storage medium may also contain one or more osmotic/oncotic stabilizer(s), free radical scavenger(s)/antioxidant(s), ion chelator(s), membrane stabilizer(s) and/or energy substrate(s).

The cell storage medium may or may not contain any organic molecules in addition to possible buffering agents, such as nutrients, serum(s) or biologically active agent(s). The cell storage medium may be protein and/or serum free medium, such as animal or human serum free medium.

A buffer solution is an aqueous solution comprising a mixture of weak acid and its conjugate base, or vice versa. Buffer solution may be used to maintain pH at substantially or nearly constant value. The pH of the cell storage medium may be in the range of 6-8, such as 7.0-7.7. Especially stem cells may require a pH range around 7.4, such as 7.2-7.6.

Examples of buffering agents useful in biological applications include TAPS ([Tris(hydroxymethyl)methylamino]propanesulfonic acid), Bicine (2-(Bis(2-hydroxyethyl)amino)acetic acid), Tris (Tris(hydroxymethyl)aminomethane) or, (2-Amino-2-(hydroxymethyl)propane-1,3-diol), Tricine (3-[N-Tris(hydroxymethyl)methylamino]-2-hydroxypropanesulfonic acid), TAPSO (3-[N-Tris(hydroxymethyl)methylamino]-2-hydroxypropanesulfonic acid), HEPES (4-(2-hydroxyethyl)-1-piperazineethanesulfonic acid), TES (2-[[1,3-dihydroxy-2-(hydroxymethyl)propan-2-yl]amino]ethanesulfonic acid), MOPS (3-(N-morpholino)propanesulfonic acid), PIPES (Piperazine-N,N'-bis(2-ethanesulfonic acid)), Cacodylate (Dimethylarsenic acid), and MES (2-(N-morpholino)ethanesulfonic acid).

One specific example of a general buffer solution is phosphate buffered saline (PBS), which usually has a pH of 7.4. It is a water-based salt solution containing disodium hydrogen phosphate, sodium chloride and, in some formulations, potassium chloride and potassium dihydrogen phosphate. The osmolarity and ion concentrations of the solutions match those of the human body, so it is isotonic.

In general the cell storage medium comprises one or more buffering agent(s). In one embodiment a cell storage medium comprises zwitterionic buffering agent, such as 4-(2-hydroxyethyl)-1-piperazineethanesulfonic acid (HEPES) which was found advantageous in the tests. The buffering agent(s) should preferably have a $pK_a$ value in the range of 6-8. The buffering agent content in the cell storage medium may be less than 100 mM, such as 10-50 mM, or 20-30 mM, for example 20-25 mM.

Other examples of zwitterionic buffering agents include 3-(N-morpholino)propanesulfonic acid (MOPS), 2-[(2-hydroxy-1,1-bis(hydroxymethyl)ethyl)amino]ethanesulfonic acid (TES), and N-(2-acetamido)-2-aminoethanesulfonic acid (ACES).

The cell storage medium may contain one or more osmotic agent(s), also called as osmotic stabilizer(s), which are used for adjusting the osmotic pressure or osmotic concentration (osmolarity) of the medium, preferably to provide isotonic solution and/or to obtain a desired osmotic pressure. Examples of osmotic agents include glucose, glucose-based polymers, starch, dextran, gelatin, albumin, amino acids, such as glutamine, polypeptides, oligopeptides, dipepdides (such as ultraglutamine), glycerol, or combinations thereof, such as glucose-based polymer(s) and amino acids, or amino acids and glycerol. These agents may also act as energy substrates. The osmotic agent(s) may be provided in a concentration in the range of 0.5-2% (w/w), such as 1-1.5% (w/w). Also ionic compounds such as salts, for example sodium chloride, may be provided as osmotic agents. The osmotic pressure of the medium may be in the range of 250-350 mOsm/kg, such as 260-320 mOsm/kg. The cell storage medium may contain one or more oncotic agent(s), also called as oncotic stabilizer(s). Oncotic pressure, or colloid osmotic pressure, is a form of osmotic pressure exerted by proteins.

The cell storage medium may also contain one or more chelating agent(s), such as ethylenediaminetetraacetic acid (EDTA), vitamin E, ultraglutamine, sodium bicarbonate, and/or one or more protease inhibitor(s).

The cell storage medium may also contain other ingredients, such as essential medium, for example minimal essential medium (MEM) or the like. Such an essential medium or minimal essential medium may be synthetic, and it may contain amino acids, salts, glucose and vitamins, and further for example sodium pyruvate, sodium bicarbonate and/or glutamine. For example Eagle's minimal essential medium (EMEM) contains amino acids, salts (calcium chloride, potassium chloride, magnesium sulfate, sodium chloride, and monosodium phosphate), glucose, and vitamins (folic acid, nicotinamide, riboflavin, $B_{12}$). Other examples of minimal essential mediums include DMEM, α-MEM, and GMEM. Dulbecco's modified Eagle's medium (DMEM) may contain amino acids (arginine, cystine, glutamine, glycine, histidine, isoleucine, leucine, lysine, methionine, phenylalanine, serine, threonine, tryptophan, tyrosine, valine), inorganic salts ($CaCl_2$), $Fe(NO_3)_3 \cdot 9H_2O$, KCl, $NaHCO_3$, $NaH_2PO_4 \cdot H_2O$), vitamins (choline, folic acid, myoinositol, nicotinamide, pantothenic acid, pyridoxine, riboflavin, thiamine), glucose and sodium pyruvate. One example of a cell storage medium contains MEM, such as DMEM, and HEPES. One example of a cell storage medium contains MEM, such as DMEM, sodium bicarbonate, HEPES, and ultraglutamine. One example of a cell storage medium contains MEM, such as DMEM, sodium bicarbonate, HEPES, fetal bovine serum (FBS) and ultraglutamine.

The present disclosure provides a method for storing eukaryotic cells, the method comprising
- providing eukaryotic cells,
- providing nanofibrillar cellulose, such as a hydrogel comprising nanofibrillar cellulose, which nanofibrillar cellulose may be at a first concentration
- combining the cells and the nanofibrillar cellulose to form a cell system, which may comprise a hydrogel wherein the nanofibrillar cellulose is at a second concentration, and storing the cell system at a temperature in the range of 0-25° C. Cell storage medium is included in the cell system. The cell system may be any cell system described herein.

The first and the second concentration, which may be also presented as consistencies and which refer to the concentration or consistency of the nanofibrillar cellulose, may be substantially same or different. For example if the cells are provided in a suspension, the second concentration may be lower than the first concentration. The first concentration may be for example in the range of 0.1-20% (w/w), such as 0.1-10% (w/w), 0.1-5% (w/w), or 0.1-2.0% (w/w)

The hydrogel may be provided in such first concentration that when combining the cells in a suspension or in the like aqueous formulation and the hydrogel, a desired second concentration is obtained, which may be in the range of 0.1-10% (w/w), such as 0.2-5% (w/w), 0.4-2% (w/w) A concentration over 0.7% (w/w), such as in the range of 0.8-1.5% (w/w), enhanced stem cell viability. In many cases a concentration in the range of 0.5-1.5% (w/w) is suitable.

The cells may be mammalian cells, such as human or animal cells. The cells may be stem cells, such as human or animal stem cells. The stem cells may be non-embryonic stem cells, such as mesenchymal stem cells, or other stem cell lines, such as human embryonic stem cell lines, generated without embryo destruction.

The cell system may contain a variety of cells, for example in a range of 0.1-10 million cells/ml gel, such as 0.5-5 million cells/ml or 1-10 million cells/ml, for example 1-3 million cells/ml. The gel concentration may be any concentration described herein, such as 0.1-10%, such as 0.2-5% (w/w), 0.4-2% (w/w), or 0.8-1.5% (w/w).

The method may comprise storing the cell system at a temperature in the range of 1-25° C., such as 1-10° C. which may be obtained in a refrigerator, or 15-25° C., such as 13-23° C. or 18-20° C. which may be ambient temperatures. The cells may be also stored at atmospheric conditions, such as at atmospheric pressure, and at atmospheric $CO_2$ or $O_2$ concentrations.

The method may comprise storing the cells in the cell system for at least 24 hours, or at least 56 or 72 hours, such as 24-52, 24-72 or 24-168 hours, even 1-21 days, such as 1-14 days or 1-7 days. Such storing may be classified as short-term storage, and it is suitable for example when cells need to be transported to another location, or if there is a pause in the use of the cells, such as during weekend or other non-working days. Storing may be also needed to enable quality control before transport and/or release.

Aqueous cell storage medium may be provided and the cell and the nanofibrillar cellulose may be combined with the cell storage medium. In one embodiment the method comprises providing cell storage medium comprising zwitterionic buffering agent, such as 4-(2-hydroxyethyl)-1-piperazineethanesulfonic acid, and combining the cells and the nanofibrillar cellulose with the cell storage medium.

The present disclosure provides a method for providing eukaryotic cells, the method comprising
  providing the cell system described herein,
  releasing the cells from the hydrogel, for example by enzymatically digesting the hydrogel or by diluting the hydrogel, to provide the cells.

The method may comprise digesting the hydrogel enzymatically with one or more cellulase(s), preferably by using a dose of 500-1500 μg enzyme/mg gel, more preferably 1000-1300 μg/mg, such as for 1-4 hours, preferably 1.5-2.5 hours. Lower doses may also be used, for example ranging up from 300 μg/mg, such as in the range of 300-1500 μg/mg or 300-1000 μg/mg. Using a lower dose of enzyme may however require more time, which may risk the viability of the cells.

One example provides a method for preparing the cell storage or cell delivery material, the method comprising providing the nanofibrillar cellulose material, which may be dewatered material, and mixing with aqueous liquid, such as cell storage medium. A mixture comprising the material is obtained. The mixture may be further combined and/or mixed with one or more auxiliary agents, such as salts, pH adjusting agents and the like.

One example provides a kit comprising a first and a second container, the first container comprising the nanofibrillar cellulose or the nanofibrillar cellulose in dehydrated form such as dry powder, concentrated granulate, or concentrated hydrogel body, and the second container comprising cellulase.

One example provides a three-dimensional discontinuous entity for storing cells comprising an aqueous medium and hydrogel bodies comprising the nanofibrillar cellulose product suspended in the aqueous medium. The aqueous medium may be cell storage medium. In one example the hydrogel bodies are interconnected. The hydrogel bodies may have a water content in the range of 1-90%, more particularly 1-50%, or 1-20%. If the material is highly dewatered, it may have a water content in the range of 0-20%, 0-10% or 1-10%, and instead of hydrogel bodies the material may be provided as nanofibrillar cellulose bodies.

The three-dimensional discontinuous entity is obtainable by a method comprising steps of providing the nanofibrillar cellulose product in a first aqueous medium to provide a hydrogel, and mixing said hydrogel with a second aqueous medium to obtain a suspension of hydrogel bodies in the second aqueous medium. The first and the second aqueous medium can be of same medium type, but they may also be different, for example the first medium being e.g. cell storage medium and the second medium being cell culture medium. The three-dimensional discontinuous entities can be made also from concentrated cellulose nanofibril hydrogels or from dry cellulose nanofibrils by granulating the concentrated hydrogel or dry cellulose nanofibrils to obtain granules, hydrating the granules in an aqueous medium, and mixing the hydrated granules, optionally adding aqueous medium, to obtain a suspension of hydrogel bodies. The discontinuous structure of the hydrogel can be verified e.g. by simple microscopic analysis or yield stress determination and comparison with the homogeneous hydrogel having the corresponding NFC concentration.

Discontinuous gel structures can be made also from concentrated (e.g. 10-30% w/w) or even from dry cellulose nanofiber products. When using dry or concentrated materials, the sample is first granulated to an appropriate size (e.g. 0.1-2 mm), hydrated in water or in cell culture medium, and then activated into either continuous or discontinuous form using appropriate methods. Spray dried particles, having an average diameter in the range of 2-20 micrometers, can be also used as a starting material. The controlled porosity in these kinds of discontinuous gels is dependent on particle size and the total concentration, i.e. distance between the swollen gel domains or gel bodies The products described herein may be provided as packed in a packing containing one or more of the products. The products may be packed in sealed packings, for example to keep them uncontaminated and to maintain moisture content, such as when the products is provided as dried or at a certain water content. When a product provided as dried or dewatered is used, it may be moisturized to a desired moisture content prior to use.

In one example the total volume of the hydrogel bodies from total volume of the three-dimensional discontinuous entity is in the range of 10-99% (v/v), such as 50-95% (v/v).

The yield stress of the three-dimensional discontinuous entity is lower than the yield stress of the corresponding continuous hydrogel in the same conditions, such as 1-95% of the yield stress of the corresponding continuous hydrogel in the same conditions.

One example provides a discontinuous three-dimensional entity and a method for producing such, wherein the method for manufacturing a three-dimensional discontinuous entity for storing cells comprises providing the nanofibrillar cellulose product in a form of
        i) a homogeneous hydrogel;
        ii) a combination of the homogeneous hydrogel with an aqueous medium; and/or
        iii) dehydrated gel bodies or dry granulated nanofibrillar cellulose product hydrated in an aqueous medium; and
    mixing at conditions favouring mechanical disruption of the homogeneous structure of the hydrogel to obtain a suspension of hydrogel bodies as a three-dimensional discontinuous entity.

One example provides a cell storage matrix. One example provides a cell system and a method for preparing a cell system, comprising providing the cell storage material disclosed herein, providing cells, providing an aqueous cell storage medium, and mixing them to obtain a cell system.

One example provides an article and use of the article for cell storage, the article comprising a substrate having a surface;
    a three-dimensional discontinuous entity comprising an aqueous medium and hydrogel bodies comprising the nanofibrillar cellulose product suspended in the aqueous medium, or a three dimensional discontinuous entity comprising an aqueous medium and hydrogel bodies comprising the nanofibrillar cellulose product suspended in the aqueous medium in a dehydrated form. The articles comprising the three-dimensional discontinuous entities may be any article suitable for storing cells, such as cell culture bottles, plates and dishes, multiwell culture plates, microtiter plates, high throughput plates and the like.

The fraction volume of the gel bodies comprising the three-dimensional discontinuous entity may vary between 50% and 99% of the total volume of the three-dimensional discontinuous entity and, accordingly, the local CNF concentration may be higher or lower than that of the total entity. The fraction of the gel bodies may be qualitatively determined readily e.g. by inspection under microscope or by sedimentation analysis.

One example provides a kit comprising a first and a second container, the first container comprising the three-dimensional discontinuous entity or the three-dimensional discontinuous entity in dehydrated form such as dry powder, concentrated granulate, or concentrated hydrogel body, and the second container comprising cellulase.

The term "three-dimensional discontinuous entity" refers to a system having three-dimensionally discontinuous structure. Said entity comprises an aqueous medium and hydrogel bodies comprising cellulose nanofibrils and/or derivatives thereof suspended in the aqueous medium.

"Discontinuous" refers to the heterogeneous structure of the entity or to interruptions in the physical continuity within the entity, for example interruptions in the aqueous medium by hydrogel bodies or interruptions in and/or between hydrogel bodies by the aqueous medium. In general the discontinuous material may comprise a plurality of separate, including partly separate, bodies, domains, granules, particles and the like, which may have substantially spherical, elliptical, or the like, or uneven shape. The plurality of bodies, domains, granules, particles and the like may be also partly interconnected in the discontinuous material. Discontinuous refers to material which is not substantially homogenous. For example a block or a membrane of hydrogel is not discontinuous, but plurality of beads, spheres or the like separate bodies suspended in liquid medium form a discontinuous entity, even if some of the bodies are attached to each other. In one embodiment the nanofibrillar cellulose is in a form of separate bodies, which may be hydrogel bodies, such as beads.

"A hydrogel body" and "a hydrogel domain" refer to an aliquot, a division, a domain, a fraction, a portion or a dose of a hydrogel, preferably having a continuous inner structure. The hydrogel body may have a well-defined, indefinite, symmetrical or asymmetrical shape.

"Suspended" or "suspension" when used in context of three-dimensional discontinuous entity or hydrogel bodies refers to a heterogeneous mixture of an aqueous medium and hydrogel wherein the hydrogel may be present as separate and/or interconnected hydrogel bodies.

"Interconnected" and "interconnection" when used in context of hydrogel bodies refers to a system where the hydrogel bodies are in contact with each other. The contact may be a direct connection between the hydrogel bodies or the hydrogel bodies may be loosely connected. When the homogeneous structure of the hydrogel is broken e.g. by mixing, the resulting discontinuous structure is characterized by hydrogel bodies of different sizes and forms. The resulting system may contain aqueous cavities between interconnected gel bodies or the loosely connected hydrogel bodies may "float" in the aqueous medium having contacts with each other. The hydrogel bodies may be indirectly connected via e.g. cells or other components present in the system.

"Dehydrated" or "dewatered" form refers to form of the material in which some but not necessarily all water is removed from the material in question. Thus, the term dehydrated encompasses e.g. concentrated slurries, granules, flakes, and powders. The dehydrated material may have a water content in the range of 0-90% (w/w), such as 0-80% (w/w), 0-50% (w/w), 1-50% (w/w), 1-40% (w/w), 1-30% (w/w), 1-20% (w/w), 10-50% (w/w), 10-40% (w/w), 10-30% (w/w), or 1-10% (w/w).

The term "kit" refers to a combination of articles or containers that facilitate a method, assay, or manipulation of the three-dimensional discontinuous entity or articles for cell storage using such. Kits may contain instructions describing how to use the kit (e.g., instructions describing the methods of the invention), cartridges, mixing stations, chemical reagents, as well as other components. Kit components may be packaged together in one container (e.g. box, wrapping, and the like) for shipment, storage, or use, or may be packaged in two or more containers.

Use of Cells

The cells included in the cell system may be transported to a site of use and provided for the use. It is possible to prepare, culture and/or provide cells at a first location, store the cells in the cell system described herein, and transport the cells in the cell system to a second location, wherein the cells may be used, studied, tested, released, administered or otherwise utilized.

The present disclosure provides a method for providing eukaryotic cells, the method comprising
providing the cell system described herein, and
releasing the cells from the hydrogel to provide the cells.

One example provides a method for transporting cells, comprising providing the cell system and transporting the cells in the cell system as disclosed herein. The cells may be released from the hydrogel by using any suitable method. In one embodiment the cells are released by enzymatically digesting the hydrogel. In one embodiment the cells are released by diluting the hydrogel. In one example the cells are released by centrifuging the hydrogel, for example though filter material. In one embodiment the cells are released by filtering the hydrogel. A combination of these method may be used, for example the hydrogel may be first enzymatically digested to weaken the gel structure, and then the gel is centrifuged and/or filtered. The hydrogel may be diluted into a concentration wherein the nanofibrillar material no longer is present as hydrogel, or the viscosity of the hydrogel has substantially lowered, so that the cells are not strongly retained in the material any more and can be easily released and recovered, for example by centrifuging and/or filtering. Cell storage medium or other suitable aqueous medium may be used for diluting the hydrogel. The nanofibrillar cellulose may be diluted to a concentration below 0.1% (w/w), below 0.05% (w/w), below 0.03% (w/w), or below 0.01% (w/w), wherein the material no longer is in a gel form, at least not in a strong gel form.

The removal of cellulose nanofibers may be carried out for example with enzyme mixtures comprising one or more enzymes, such as some or all necessary enzymes for partial or total degradation of cellulose molecules as well as other wood derived components in it, such as hemicelluloses. Examples of the enzymes include exocellulases, such as exoglucanases, and endocellulases, such as endoglucanases. Further examples include designed enzyme mixtures for the NFC in question and commercially available cellulase-hemicellulase preparations. The composition of the mixture can vary depending on the chemical composition of the raw material used for production of that NFC. For example when birch pulp is used for production of NFC the mixture includes at least intact endo- and exocellulases or parts thereof, endo-xylanases and 13-D-glycosidases and 13-D-xylosidases. For hydrolysis of softwood-derived NFC the mixture needs to be supplemented at least with endomannanases and 13-D-mannosidases. The benefit of designed mixtures pooled from purified enzyme components is that they do not contain additional proteins or other unwanted components, such as side activities, debris from the cultivation organism or residues from culture broth, which is often the case for commercial enzyme preparations. Especially harmful is, if the preparation contains proteases, which might attack on the cell surfaces. Commercial enzyme mixtures designated for total hydrolysis of plant based materials can also be used in hydrolysis of NFC, but more preferably after at least crude purification step, such as gel filtration or dialysis. Regardless of the enzyme preparation, either a designed or commercial mixture, the components are selected so that they can optimally hydrolyse NFC for example in respect of pH, temperature and ionic strength. Commercial preparations are available, which are acting either in the acidic pH values (pH 3.5-5) or basic pH values (pH 6-8) and at temperatures from room temperature up to 60-80° C. Very often the cells are grown at 37° C., which is an optimal temperature for the most cellulases and hemicellulases. The cell lines may be also genetically engineered to produce the needed enzyme protein(s) into the storage system.

One example provides a method for removing the nanofibrillar cellulose product from a cell system, the method comprising
providing a cell system, such as cell storage material containing cells;
diluting said cell system with aqueous or nonaqueous liquid;
optionally centrifuging the cell system to sediment the cells and cell aggregates;
removing nanofibrillar cellulose product, for example by decantation.

One example provides a method for removing the nanofibrillar cellulose product from a cell system, the method comprising
providing a cell system,
contacting the cell system with an enzyme capable of degrading the nanofibrillar cellulose material;
optionally centrifuging the cell system to sediment the cells and cell aggregates;
removing nanofibrillar cellulose product, for example by decantation. Preferably nanofibrillar cellulose product to be removed is enzymatically degraded to obtain at least partly and preferably mostly degraded nanofibrillar cellulose product.

The cells release from the cell system may be recovered and used. The use of the cells may be medical use, for example the cells may be used in a therapeutic method comprising administering the cells to a patient in need of therapy. The use may be also scientific, research or test use. The cells may be for example applied to a test system and/or to a cell culture. Different uses may require a different medium. For example serum free medium, such as fetal bovine serum (FBS) free medium, may be used for cell for therapeutic applications.

Especially stem cells may be used in therapeutic methods, such as in cell-based therapy. The therapeutic method may comprise stem cell transplantation. The cells may be provided to release agents, such as paracrine factors that may promote wound healing and tissue regeneration, or the cells may be provided to differentiate into desired cells at a target. During storing the cells are maintained in an undifferentiated state, and when release and applied to a target, which may be in a patient, the cells begin and/or are arranged to differentiate. Further agents may be provided to initiate this process.

The present application provides medical products including the cells, which may be applied onto the skin or other tissue of a target or a subject, such as a patient or a person, human or animal, suffering from a condition. The medical products may be provided as gels, patches, plasters, bandages or the like, which may be applied onto a wound or onto damaged area or onto an area or a target requiring treatment. Such products may also include other materials, such as one or more gauzes or the like reinforcing material.

The medical products may contain only one layer of nanofibrillar cellulose, or they may contain one or more additional layers, which may be nanofibrillar cellulosic layers and/or other layers. The nanofibrillar cellulose may be incorporated in a gauze, such as nonwoven. In one embodiment the medical product comprises a gauze, such as nonwoven. The gauze may be included or incorporated in the product in any suitable manner described herein. The moisture content of the combination may be in the same range as discussed in previous. In one example the nanofibrillar cellulose in a layer may have a moisture content in the range of 80-99.9% (w/w), or 50-99.8% (w/w), such as in the range of 90-99.8% (w/w), especially when incorporated with a gauze.

The therapeutic methods wherein the stem cells may be used, are various and include for example tissue regeneration, cardiovascular disease treatment, brain disease treatment, such as Parkinson's and Alzheimer's disease treatment, cell deficiency therapy, such as in type I diabetes, blood disease treatments, such as providing hematopoietic stem cells for treating leukemia, sick cell anemia and other immunodeficiency problems.

The present disclosure also provides use of the nanofibrillar cellulose matrices and the cell systems disclosed herein for the methods disclosed herein.

One embodiment provides use of the cells system disclosed herein for transporting, providing delivering and/or administering cells. One example provides use of the cell storage materials or cell systems disclosed herein for storing cells. One example provides use of the cell storage materials or cell systems disclosed herein for quality control of the cells.

The present disclosure provides the cell system disclosed herein for use in therapeutic methods, such as methods disclosed herein, for example in therapeutic method comprising administering the cells.

EXAMPLES

Preparation of Cell System
Prior to Storage:

Human mesenchymal stem cells (MSCs) were grown as normal prior to storage on tissue culture plastic in FBS-containing medium, and passaged using trypsin/EDTA according to the protocol disclosed by Rafiq et al. "A quantitative approach for understanding small-scale human mesenchymal stem cell culture—implications for large-scale bioprocess development", Biotechnology Journal, Special Issue: Stem cell engineering, April 2013, p. 459-471 (https://doi.org/10.1002/biot.201200197).

For Storage:

Plates used were ultra-low attachment (ULA) well-plates, typically 24 well plates Temperatures used:

Refrigerated: 4° C. (range 3-6° C.). Normal lab fridge, plates stored inside a plastic box so no atmospheric control Ambient: 18-22° C. Stored in storage cupboard, again inside plastic box so no atmospheric control 37° C.: used as controls in standard tissue culture incubator with 5% $CO_2$ and humidified.

Pausing Medium used:
50 ml of 10×DMEM
425 ml of distilled/sterile water.
14.75 ml of 7.5% sodium bicarbonate solution
12.5 ml of 1 M HEPES solution
55 ml of FBS
5.5 ml of ultraglutamine.

This was sterile filtered and stored in the fridge.

Nanofibrillar cellulose (GrowDex®) and cellulase preparation (GrowDase™®) were provided by UPM. GrowDex® was prepared as per UPM instructions by diluting with pausing medium until required concentration of gel was achieved. The range of concentrations tried were in the range of 0.4-0.9% (w/w), which had impact on recovery using cellulase.

Cells: hMSCs (original source Lonza, bone marrow derived mononuclear cells) were used. Ranges of seeding densities were tested.

Seeding of GrowDex® with cells. To seed 1 million cells/ml of diluted hydrogel (gel % 0.8). All work was done in biological safety cabinet at ambient temperature. $1 \times 10^6 * 0.380 = 3.8 \times 10^5$ cells per well.

Total amount of cells to be mixed with 0.8% GrowDex®=6 wells*$3.8 \times 10^5$ cells=$2.28 \times 10^6$ cells.

Resuspend $2.28 \times 10^6$ cells in 2.28 ml of GrowDex® medium.

In Plate: 24-well ULA plate 380 µl of cells/GrowDex® were applied into each of the 3 wells. Each well was topped up with medium to 1 ml and transferred to appropriate storage condition (this cooling process was not controlled unlike in freezing).

Cell Recovery:

Hydrogels were digested as per the protocol (instructions for use of GrowDase®) provided by UPM. The enzyme was diluted to right concentration, added on top of hydrogel, and left at 37° C. for incubation period under static conditions. Different concentrations of enzyme and different times were tested. Once cells were recovered and washed, they were diluted in normal culture medium before seeding into normal tissue culture plates for further analysis. Cells shift from ambient/refrigerated temp to 37° C. was not controlled during recovery phase.

Evaluation of the Cell Systems

Tests were carried out to investigate whether the cell system would be able to support the longer-term (e.g. ≥1 week) storage and transportation of mesenchymal stem cells (MSCs) at ambient and refrigerated conditions in order to provide an alternative to cryopreservation for the storage and transport of clinically relevant cell types.

It was tested whether GrowDex® hydrogel supports hypothermic storage of MSCs under either ambient or refrigerated conditions. It was found out that GrowDex® is a suitable hydrogel structure for storage of cells at refrigerated or ambient temperatures.

Figure 2:
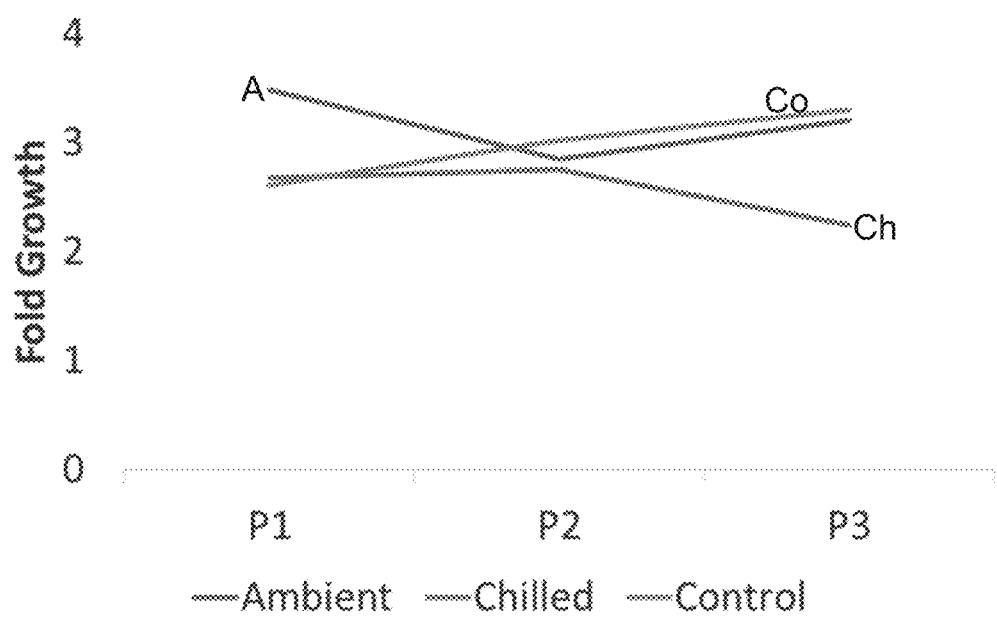
FIG. 2 shows MSCs paused at ambient A) or refrigerated (Ch) conditions for up to 72 hours and subsequently plated onto tissue culture plastic retain the ability to grow over the 3 passages tested. Control (Co) is cells maintained as per standard culture conditions.

MSCs can be stored in GrowDex® at ambient (~18-20° C.) and refrigerated temperatures for at least up to 72 hours. Cells recovered from the gels showed ~90% or ~70% viability following 72 hours storage at ambient and refrigerated temperatures respectively (FIG. 1) and retained the ability to grow once re-plated (FIG. 2). However, overall yield (% of live cells/original seeding density) was ~50% and when testing was extended to 7 days, it dropped as low as 20% under refrigerated conditions.

The impact of cell density on protocol success was also tested. It was found out that GrowDex® can store cells at sufficiently high densities for clinical or seed-train bioreactor seeding.

Initial experiments indicated that GrowDex® was able to support cells for at least 24 hours at up to $3 \times 10^6$ cell per well of a 96-well plate although this was dependent on the gel stiffness (Table 1). This indicated that MSCs preferred a stiffer gel.

TABLE 1

MSCs paused for 24 hours at ambient
temperature and then recovered from
the gels were assessed for viability using
a NucleoCounter ® automated cell counter.

| Gel % | Seeding density | Viability % |
|---|---|---|
| 0.4 | $1 \times 10^6$ | 56.9 |
|  | $2 \times 10^6$ | 46.5 |
|  | $3 \times 10^6$ | 48.5 |
| 0.7 | $1 \times 10^6$ | 56.5 |
|  | $2 \times 10^6$ | 51.6 |
|  | $3 \times 10^6$ | 48.6 |
| 0.9 | $1 \times 10^6$ | 91 |
|  | $2 \times 10^6$ | 94.6 |
|  | $3 \times 10^6$ | 93.1 |

The impact of the cell recovery period on cell viability was tested. The focus remained on the gel digestion phase. Initial work with gels of 0.4-0.9% yielded poor cell viability (<85%) and yields (as low as <15%) with long (24 hour, 300 µg/mg GrowDase®) digestions required to digest the gels. Although cells recovered were able to grow on normal tissue culture plastic it was noted that some appeared to grow out of colonies, almost like an explant, rather than a homogenous monolayer as expected and this was likely the result of the cell aggregation noted at the end of the 24 hours especially at the higher gel concentrations (FIG. 3).

Figure 3A:
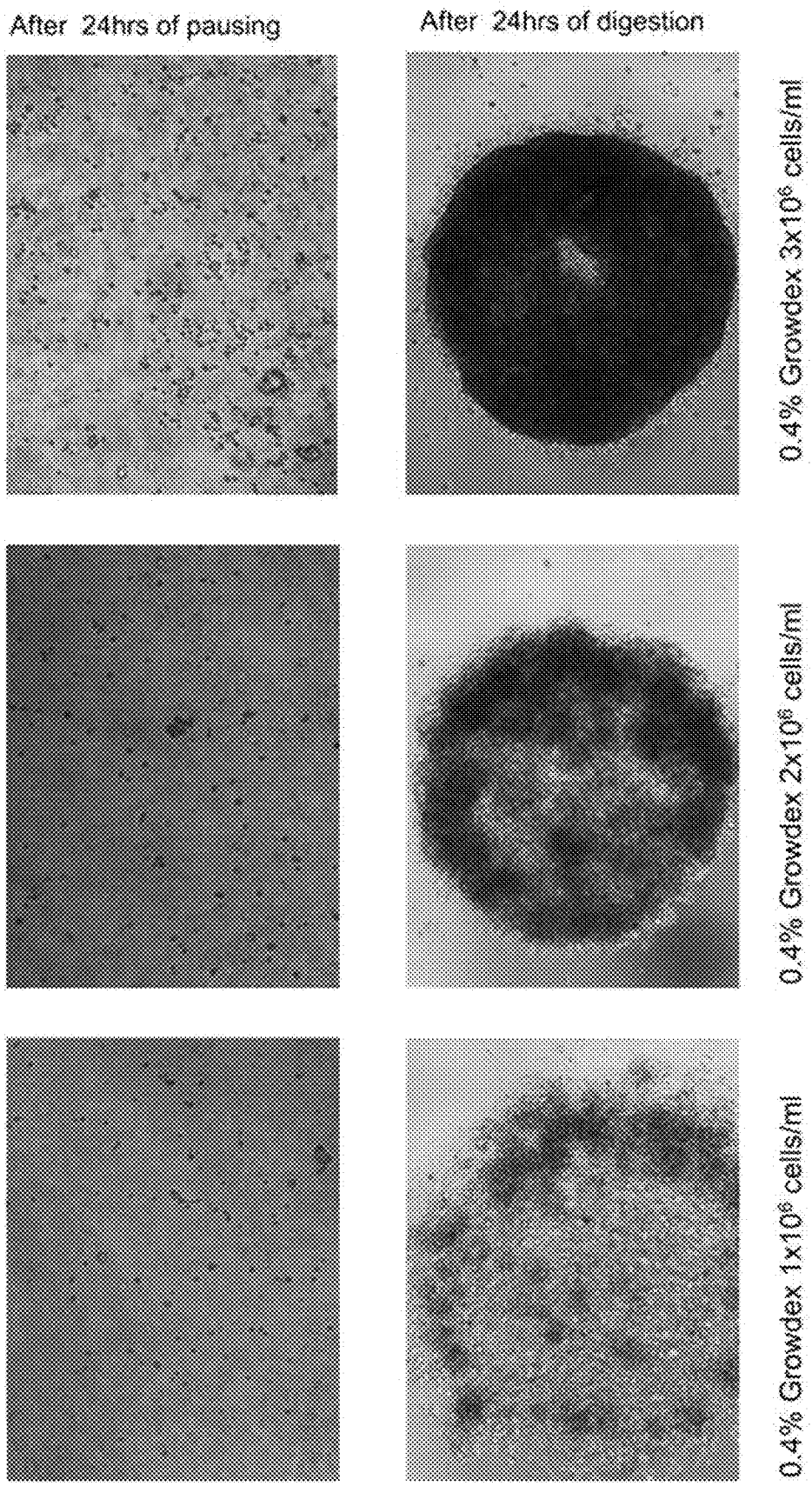
FIG. 3A shows a representative image of MSCs paused at ambient temperature in 0.4% GrowDex® at different cell densities for 24 hours and then digested for 24 hours (300 µg/mg GrowDase®).
Figure 3B:
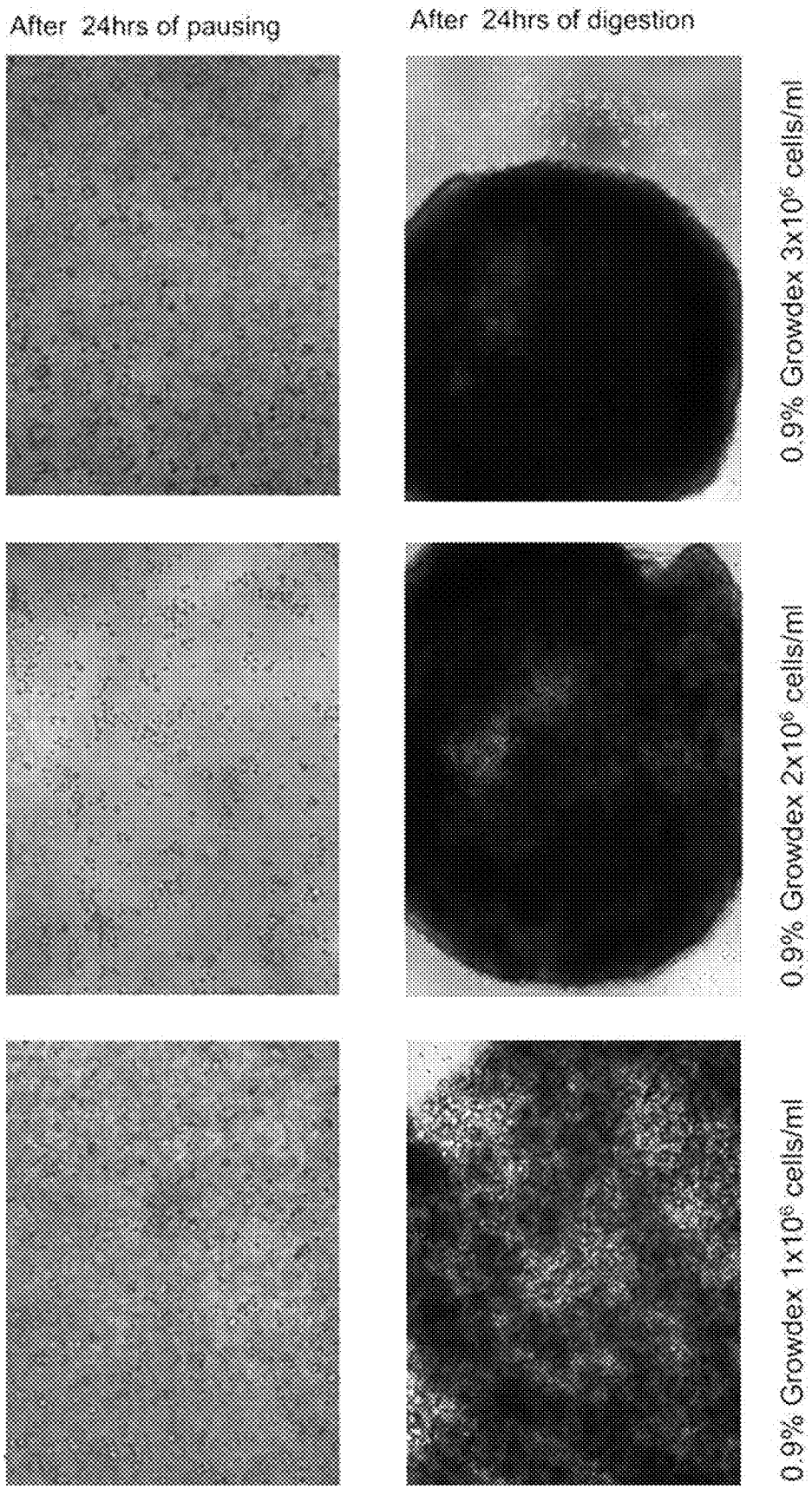
FIG. 3B shows a representative image of MSCs paused at ambient temperature in 0.9% GrowDex® at different cell densities for 24 hours and then digested for 24 hours (300 µg/mg GrowDase®).

FIG. 3 shows images of MSCs paused at ambient temperature in 0.4% (A) and 0.9% (B) GrowDex® at different cell densities for 24 hours and then digested for 24 hours with 300 µg/mg GrowDase®.

Figure 4:
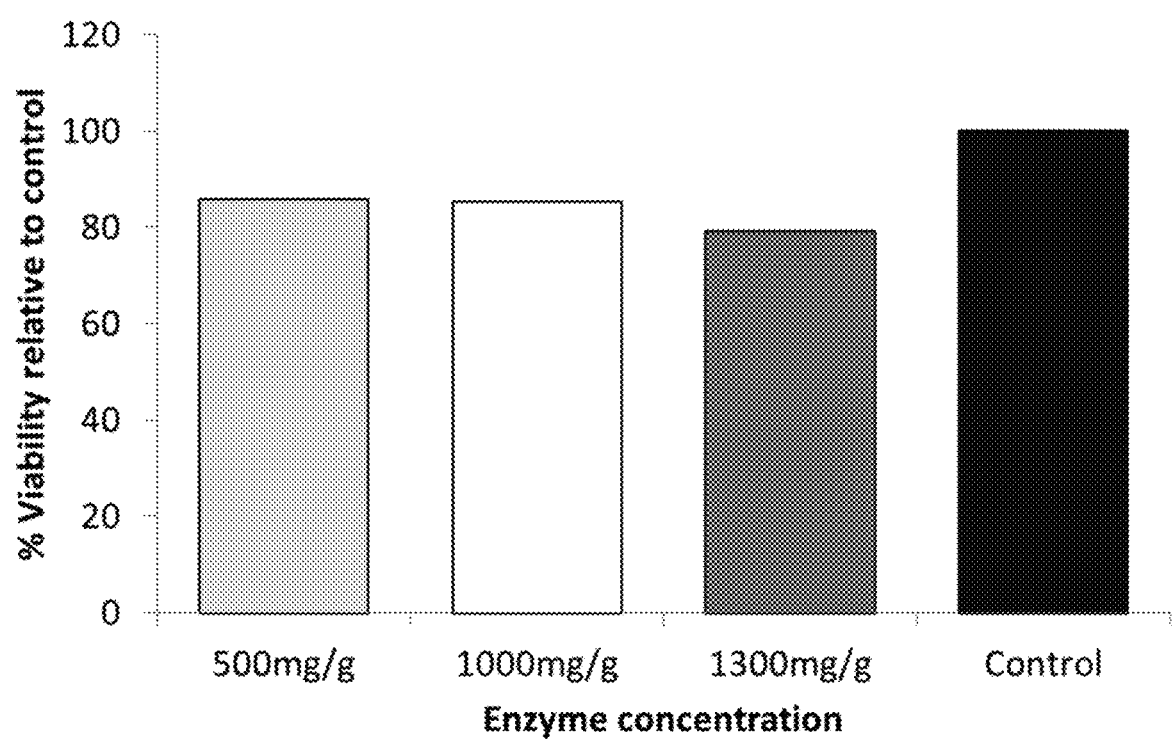
FIG. 4 shows the viability of MSCs exposed to the enzyme as assessed by PrestoBlue™ cell viability reagent showing that cells were able to retain metabolic function and not just membrane integrity.

Experiments using higher GrowDase® concentrations and shorter digestion times resulted in a higher yield of viable cells (Table 2) and cells grew into a more homogenous monolayer. All results were similar indicating that depending on whether cost or time was a key driver, either a 2 or 4 hour digestion with 500-1300 µg/mg (mg/g) GrowDase® is possible. FIG. 4 shows that cell viability was not impacted by higher enzyme concentrations.

TABLE 2

Data from experiments using higher GrowDase ® concentrations and shorter digestion times. N = 3.

|  | Enzyme concentration µg/mg | Average viability % | Total cells | Seeding density/gel | Average yield % |
|---|---|---|---|---|---|
| 2 h digestion | 1000 | 92 | $2.3 \times 10^5$ | $4 \times 10^5$ | 57 ± 3 |
| 2 h digestion | 1300 | 92 | $2.6 \times 10^5$ | $4 \times 10^5$ | 64 ± 7 |
| 4 h digestion | 500 | 90 | $2.3 \times 10^5$ | $4 \times 10^5$ | 58 ± 5 |

MSCs can be stored in GrowDex® at ambient (~18-20° C.) and refrigerated temperatures for up to 72 hours. Cells recovered from the gels showed ~90% or ~70% viability following 72 hours storage at ambient and refrigerated temperatures respective and retained the ability to grow once re-plated.

The invention claimed is:

1. A cell system comprising eukaryotic cells at a paused state in a hydrogel comprising nanofibrillar cellulose in cell storage medium at a temperature in the range of 1-25° C.
2. The cell system of claim 1, wherein the cell storage medium comprises zwitterionic buffering agent.
3. The cell system of claim 1, wherein the cell storage medium comprises one or more osmotic agent(s).
4. The cell system of claim 1, wherein the cells are stem cells.
5. The cell system of claim 1, wherein the nanofibrillar cellulose is in a form of separate bodies.
6. The cell system of claim 1, wherein the nanofibrillar cellulose, when dispersed in water, provides yield stress in the range of 1-50 Pa, determined by rotational rheometer at a consistency of 0.5% (w/w) by weight in aqueous medium at 20° C.±1° C., and/or has an average diameter of a fibril of 200 nm or less.
7. The cell system of claim 1, wherein the concentration of the nanofibrillar cellulose in the hydrogel is in the range of 0.1-10% (w/w).
8. The cell system of claim 1, wherein the nanofibrillar cellulose is selected from anionically modified nanofibrillar cellulose, cationically modified nanofibrillar cellulose, unmodified nanofibrillar cellulose, and oxidized nanofibrillar cellulose.
9. The cell system of claim 1, wherein the eukaryotic cells are mammalian cells.
10. The cell system of claim 1, wherein the concentration of the nanofibrillar cellulose in the hydrogel is in the range of 0.5-1.5% (w/w).
11. The cell system of claim 1, wherein the cells are at an undifferentiated state.
12. A method for storing eukaryotic cells, the method comprising
providing eukaryotic cells,
providing nanofibrillar cellulose,
providing cell storage medium,
combining the cells, the nanofibrillar cellulose and the cell storage medium, and
storing the cell system at a temperature in the range of 1-25° C. to form the cell system of claim 1.
13. The method of claim 12, comprising storing the cell system at a temperature in the range of 15-25° C.
14. The method of claim 12, comprising storing the cells in the cell system for at least 24 hours.
15. A method for providing eukaryotic cells, the method comprising
providing the cell system of claim 1,
releasing the cells from the hydrogel to provide the cells.
16. The method of claim 15, comprising digesting the hydrogel enzymatically with one or more cellulase(s).
17. A method for transporting cells, the method comprising
providing the cell system of claim 1, and
transporting the cells in the cell system.
18. A therapeutic method comprising
providing the cell system of claim 1, and
administering cells from the cell system to a patient in need of therapy.

* * * * *